United States Patent
Kato et al.

(10) Patent No.: US 7,067,618 B1
(45) Date of Patent: Jun. 27, 2006

(54) MEDICINAL PREPARATIONS

(75) Inventors: Yasuki Kato, Susono (JP); Hiroko Kusano, Sunto-gun (JP); Yuji Kawaguchi, Tagata-gun (JP); Kunio Ito, Shizuoka (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/869,049

(22) PCT Filed: Dec. 24, 1999

(86) PCT No.: PCT/JP99/07278

§ 371 (c)(1),
(2), (4) Date: Jun. 22, 2001

(87) PCT Pub. No.: WO00/38736

PCT Pub. Date: Jul. 6, 2000

(30) Foreign Application Priority Data

Dec. 24, 1998 (JP) .................. PCT/JP98/05857

(51) Int. Cl.
*C07K 38/28* (2006.01)
*C07K 17/04* (2006.01)
*C07K 17/08* (2006.01)
*A61K 38/00* (2006.01)
*A61K 38/14* (2006.01)

(52) U.S. Cl. .................... 530/303; 300/322
(58) Field of Classification Search .......... 424/400, 424/450
See application file for complete search history.

(56) References Cited

U.S. PATENT DOCUMENTS 5,580,543 A * 12/1996 Sessler et al. ............ 424/9.34
5,723,121 A    3/1998 Takenaga et al.

FOREIGN PATENT DOCUMENTS

| JP | 07-061999 | 7/1995 |
|----|-----------|--------|
| JP | 09-263579 | 7/1997 |
| WO | WO9003401 | 4/1990 |
| WO | WO9601639 | 1/1996 |
| WO | WO9823625 | 6/1998 |

OTHER PUBLICATIONS

Stedman's Medical Dictionary, 1995, Williams and Wilkins, Baltimore. p. 1223, col. 1, Lines 61-64.*
G. Wilson, "Effect Of Reductive Lactosamination On The Hepatic Uptake Of Bovine Pancreatic Ribonuclease A Dimer", vol. 253, No. 7, Apr. 10, 1978, pp. 2070-2072.
Inoue, et al., "Synthesis Of A Superoxide Dismutase Derivative That Circulates Bound To Albumin And Accumulates In Tissues Whose pH Is Decreased", Biochemistry 1989, 28, 6619-6624.
Patent Abstracts of Japan, Pub. No. 07-061999, pub. Jul. 3, 1995.
Patent Abstracts of Japan, Pub. No. 09-263579, pub. Jul. 10, 1997.
Rogers, et al., "Hepatic Uptake Of Proteins Coupled To Fetuin Glycopeptide", vol. 45, No. 3, 1971, pp. 622-629.
Schmer, et al., "Kinetics Of Uptake And Activity In Mouse Liver Of Glutaminase Coupled To Desialated Orosomucoid", 538 (1978), pp. 397-405.
Fiume, et al., "Lactosaminated Human Serum Albumin As Hepatotropic Drug Carrier", vol. 146, No. 1, Sep. 1982, pp. 42-46.
Fiume et al., "A Chemically Stable Conjugate Of 9-β-D-Arabinofuranosyl-Adenine 5'-Monophosphate With Lactosaminated Albumin Accomplishes A Selective Delivery Of The Drug To Liver Cells", vol. 35, No. 6, pp. 967-972, 1986.
Marsh, et al., "Glycosylation Of *Escherichia coli* L-Asparaginase", vol. 252, No. 21, pp. 7678-7684, 1977.
G. Wilson, "Effect Of Reductive Lactosamination, On The Hepatic Uptake Of Bovine Pancreatic Ribonuclease A Dimer", vol. 253, No. 7, Apr. 10, 1978, pp. 2070-2072.

* cited by examiner

*Primary Examiner*—Jon Weber
*Assistant Examiner*—Kailash C. Srivastava
(74) *Attorney, Agent, or Firm*—Antonelli, Terry, Stout and Kraus, LLP.

(57) ABSTRACT

The present invention provides a pharmaceutical preparation comprising a compound which can be obtained by reacting a compound having a free amino group with a sugar having the reducing power. The preparation is capable of improving the in vivo durability of various compounds and releasing the compounds in response to changes in pH, and thus is useful for causing the compounds to act specifically on target parts.

21 Claims, No Drawings

MEDICINAL PREPARATIONS

TECHNICAL FIELD

The present invention relates to pharmaceutically useful preparations designed for altering the in vivo behavior of pharmaceutical compounds so as to efficiently secure their effects.

BACKGROUND ART

Peptides and proteins have been widely utilized as pharmaceuticals. It is known to chemically modify pharmaceuticals such as peptides and proteins with polyethylene glycol, dextran, polyamino acids, albumin, inulin, etc. in order to prolong their action in vivo.

On the other hand, attempts have been made to develop targeting preparations of pharmaceuticals such as peptides and proteins. For example, it is reported that the modification of lysozyme and albumin [J. C. Rogers and S. Kornfeld, Biochem. Biophys. Res. Commun., 45, 622 (1971)] and glutaminase [G. Schemer et al., Biochem. Biophys. Acta, 538, 397 (1978)] with asialoglycoproteins is effective for targeting of these substances towards liver. It is also observed that the chemical modification of albumin [L. Fuime et al., FEBS Lett., 146, 42 (1982), L. Fuime et al., Biochem. Pharmacol., 35, 967 (1986)], L-asparaginase [J. W. Marsh et al., J. Biol. Chem., 252, 7678 (1977)] and ribonuclease [G. Wilson, J. Biol. Chem., 253, 2070 (1977)] with lactose enhances the accumulation of these substances at liver. Chemical modification techniques useful in such targeting include the carbodiimide method, the glutaraldehyde method, the SPDP (N-succinimidyl-3-(2-pyridyldithio)propionate) method, the active ester method and the reduction method using sodium cyanoborohydride. The compounds prepared by chemically modifying pharmaceuticals such as peptides and proteins using these techniques are gradually decomposed in vivo to release the pharmaceuticals, but they can not be expected to rapidly release the pharmaceuticals in response to changes in pH or the like.

It is known that the pH of interstitium is lowered to a level of 6.9 in cancer cells etc. and that administration of glucose lowers the pH of interstitium from 6.9 to 6.2 [H. Kahler and W. V. Robertson, J. Natl. Cancer Inst., 3, 495 (1943), P. M. Gullino et al., J. Natl. Cancer Inst., 34, 857 (1965)]. It is also known that inflamed parts have a pH in the acidic range, i.e. pH 6.5 [V. Menkin, Biochemical Mechanism in Inflammation, Thomas, Springfield, III, pp. 69–77 (1956)]. Further, it has been experimentally demonstrated that transient ischemia in rats lowers the pH of the affected part from 7.4 to 6.5 [N. Watanabe et al., Biochem. Pharmacol., 38; 3477 (1989)]. Also known is a pH-sensitive drug delivery system (DDS) for superoxide dismutase (SOD) using a styrene-maleic acid copolymer (SM) [Biochemistry, 28, 6619 (1989), Biochem. Pharmacol., 38, 3477 (1989)]. In this DDS, superoxide dismutase covalently binds to the styrene-maleic acid copolymer (SM-SOD) noncovalently binds to the warfarin site on albumin in blood at pH around neutrality. As the pH is lowered, SM is protonated and the albumin-binding ability thereof is decreased to cause release of SM-SOD.

It is also known that epidermal growth factor (EGF) receptor is excessively expressed at squamous cell carcinoma [S. Ogawa et al., Jpn. J. Cancer Res., 79, 1201 (1988)], and based on this fact, targeting therapy using a carcinostatic agent together with anti-EGF receptor antibody has been attempted [E. A. Pirak et al., Proc. Natl. Acad. Sci. USA, 86, 3778 (1989)]. Tsuchiya et al. have found that by binding EGF to the surface of liposome, the liposome is incorporated into cancer cells via the EGF receptor [S. Tsuchiya et al., Drug Delivery System, 4, 193 (1989)]. However, the EGF receptor is expressed also in normal cells, and it is difficult to specifically target diseased parts.

DISCLOSURE OF THE INVENTION

An object of the present invention is to provide a pharmaceutical preparation (a pH responsive pharmaceutical preparation) which is capable of rapidly releasing a compound having a free amino group such as an amino acid derivative, a peptide, a protein or an enzyme in response to changes in pH at focuses by reacting the compound having a free amino group with a sugar having the reducing power. The pharmaceutical preparation of the present invention is capable of releasing various compounds having a free amino group in response to changes in pH and releases such compounds specifically at target parts at which the pH is lowered due to the occurrence of inflammation, tumor or the like to cause the compounds to exhibit their effects. The preparation releases the above compounds nowhere except at target parts, which is expected to result in reduction of side effects. Further, when administered in vivo, the pharmaceutical preparation of the present invention alters the in vivo behavior of the compounds as compared with that of the unmodified compounds, whereby effects such as improvement of durability in blood can be expected. It is also expected that the addition of a specific sugar enables the specific recognition of the sugar receptor, for example, galactose receptor and then the release of the sugar in response to the pH lowering in an endosome formed after the endocytosis by a cell to release a free pharmaceutical compound into the cell.

The present invention relates to a pharmaceutical preparation comprising a compound which can be obtained by reacting a compound having a free amino group with a sugar having the reducing power.

There is no specific restriction as to the compounds having a free amino group to be used in the present invention. Suitable compound include pharmaceutical compounds, for example, peptides, proteins and enzymes such as bradykinin, angiotensin, anthriopeptin, oxytocin, vasopressin, adrenocorticotropin (ACTH), calcitonin, insulin, glucagon, cholecystokinin, β-endorphin, melanocyte-inhibiting factor, melanocyte-stimulating hormone, gastrin antagonist, neurotensin, somatostatin, brucine, cyclosporin, enkephalin, transferrin, RGD peptide, thyroid hormone, growth hormone, gonadotropic hormone, luteinizing hormone (LHRH), asparaginase, arginase, uricase, carboxypeptidase, glutaminase, SOD, tissue plasminogen activator (t-PA), streptokinase, interleukin, interferon, muramyl dipeptide, thymopoietin, granulocyte colony-stimulating factor (G-CSF), granulocyte macrophage colony-stimulating factor (GM-CSF), erythropoietin-(EPO), thrombopoietin (TPO), trypsin inhibitor, lysozyme, EGF, insulin-like growth factor (IGF), nerve growth factor (NGF), platelet-derived growth factor (PDGF), transforming growth factor (TGF), endothelial cell growth factor (ECGF), fibroblast growth factor (FGF), glia cell growth factor (GGF), thymosin and specific antibodies (e.g., anti-EGF receptor antibody); carcinostatic agents such as doxorubicin derivatives [e.g., 3'-(D-Val-Leu-Lys)-doxorubicin], 5-fluorouracil derivatives [e.g., L-Ala-2-(5-fluorouracil-1-yl)-Gly], daunorubicin, idarubicin and neocarzinostatin; amino acid derivatives such as dopamine; amoxicillin, ampicillin, amantadine hydrochloride, epirubicin hydrochloride, doxorubicin hydrochloride, dopamine hydrochloride, vancomycin hydrochloride, talampicillin hydrochloride, bacampicillin hydrochloride, cycloserine, ciclacillin, cefaclor, cefatrizine, cefadroxil, cefalexin, cefradine, cefroxadine, tranexamic acid, norepinephrine, methyldopa, melphalan, liothyronine sodium, astromicin sulfate, isepamicin sulfate, kanamycin sulfate, micronomicin sulfate, sisomicin sulfate, dibekacin sulfate, arbekacin sulfate, neomycin sulfate, netilmicin sulfate, paromomycin sulfate, bleomycin sulfate, levodopa, and antibody drugs [e.g., human serum immunoglobulins (e.g., pepsin-treated human serum immunoglobulin, plasmin-treated human serum immunoglobulin, β-propiolactone-treated human serum immunoglobulin, S-alkylated human serum immunoglobulin, S-sulfonated human serum immunoglobulin and polyethylene glycol-treated human serum immunoglobulin), mouse monoclonal antibodies, human monoclonal antibodies, chimera antibodies, anti-idiotype antibodies and Fab fragments comprising variable region only].

Preferred compounds having a free amino group are peptides, proteins and enzymes such as insulin, transferrin, asparaginase, SOD, t-PA, interferon and specific antibodies, and pharmaceutical compounds such as doxorubicin hydrochloride, epirubicin hydrochloride and bleomycin sulfate.

In the present invention, any sugars having the reducing power can be used. Suitable sugars include glucose, lactose, fucosylglucose, galactosyllactose, fucosyllactose, lacto-N-tetraose, lacto-N-hexaose, lacto-N-neohexaose, dimannosyl-N-acetylglucosamine, sialyllactose such as 3'-sialyllactose and 6'-sialyllactose, disialyllactose, N,O-diacetylneuraminyllactose, 3'-sialyllactose 6'-sulfate, lactose 6'-sulfate, lactose 3'-phosphate, disialyllacto-N-tetraose and glycolipids. Also useful are compounds prepared by chemically binding a polymer (e.g., polyoxyethylene, polyglutamic acid and polyvinylpyrrolidone) to hydroxyl groups other than the hydroxyl group formed from the reducing aldehyde group (i.e., the hydroxyl group of the hemiacetal moiety) in the above compounds. The reducing aldehyde group in the sugar chain of the sugar having the reducing power reacts with the amino group of the compound having a free amino group to give a compound in which the sugar chain is bound to the amino group moiety of the compound having a free amino group.

Examples of the preferred sugars are sialyllactose, lactose, glucose and disialyllactose.

Examples of the compounds which can be obtained by reacting a compound having a free amino group with a sugar having the reducing power and which are capable of rapidly releasing the compound having a free amino group in response to changes in pH include Schiff bases and aminals.

The compound having a free amino group, the sugar having the reducing power, and the compound which can be obtained by reacting a compound having a free amino group with a sugar having the reducing power may be modified with pharmaceutical carriers such as liposome, lipid emulsion, microemulsion, polymer micelle, microcapsule, microsphere or a magnetic particle. The compound having a free amino group, the sugar having the reducing power, and the compound which can be obtained by reacting a compound having a free amino group with a sugar having the reducing power may also be included in the pharmaceutical carriers. The compound having an amino group to be modified with or included in the pharmaceutical carriers can be the above-mentioned pharmaceutical compounds or compounds having an amino group without any particular pharmacological activities. In addition to the compounds having a free amino group such as the above-mentioned pharmaceutical compounds, any compounds having pharmacological activities may be included in the pharmaceutical carriers.

Examples of the preferred pharmaceutical carriers are liposome, lipid emulsion and polymer micelle.

The pharmaceutical preparation of the present invention can be produced by adding 1 to 10000 parts by weight, preferably 10 to 1000 parts by weight of the sugar having the reducing power to 1 part by weight of the compound having a free amino group, which may be modified with the pharmaceutical carrier, and subjecting them to reaction by allowing them to stand in an aqueous solution of pH 7 to 14, preferably pH 7.5 to 10, at 0 to 100° C., preferably 20 to 50° C., for one minute to one month, preferably 1 to 96 hours. The pH adjustment may be carried out by using any suitable substance, for example, phosphate buffer or sodium hydroxide.

The product obtained by the above process can be used as such, as the pharmaceutical preparation of the present invention. The product may also be freeze-dried together with excipients such as mannitol, lactose or glycine according to the aimed use, storage conditions, etc. When the preparation is stored in freeze, cryoprotectants such as glycerin may be added.

The pharmaceutical preparation of the present invention is generally used as an injection, but may also be formed into preparations for oral administration, nasal administration, ophthalmic administration or percutaneous administration, a suppository, an inhalation, etc.

The pharmaceutical preparation of the present invention administered in vivo alters the in vivo behavior of the pharmaceutical compound contained therein as compared with that of the unmodified compound, and thereby gives effects such as improvement of the durability of the compound in blood or specific binding of the compound to the galactose receptor in liver. When a compound having anti-tumor activity is used in the pharmaceutical preparation of the present invention, the compound is released from the sugar in the neighborhood of a tumor focus due to the pH lowering around the tumor focus and thus acts directly upon tumor cells without injuring cells other than the tumor cells, whereby the production of side effects of the compound can be prevented. When an anti-EGF receptor antibody is used in the pharmaceutical preparation of the present invention, the antibody modified with the sugar does not bind to the EGF receptor in normal cells, but in the neighborhood of a tumor, the sugar is released from the preparation due to the pH lowering, thus enabling the anti-EGF receptor antibody to be released and to give its effect on tumor cells.

Examples and test examples of the present invention are shown below.

BEST MODES FOR CARRYING OUT THE INVENTION

Example 1

A solution of 0.2 mg of bovine pancreatic insulin (Wako Pure Chemical Industries, ltd.) in 1 mL of a 2 mmol/L aqueous solution of hydrochloric acid, a solution of 320 mg of anhydrous β-lactose (Nacalai Tesque, Inc.) in 2 mL of distilled water, and 1 mL of a 200 mmol/L phosphate buffer (pH 8.4) were mixed in a test tube to give a mixture having a pH of about 8.1. The test tube was put into a constant temperature water bath at 40° C. to cause reaction. The reaction mixture was sampled after 0, 5 and 24 hours, and analyzed for products obtained by the reaction of insulin with lactose by high performance liquid chromatography (HPLC) under the following conditions.

Column: YMC-Pack ODS-A or YMC-Pack ODS-AM, 6.0×150 mm

Mobile phase: 100 mmol/L phosphate buffer (pH 8.0) containing 0.001% Triton X-100: acetonitrile containing 0.001% Triton X-100=25 parts by volume: 9 parts by volume Flow rate: 1.3 mL/minute Detection wavelength: 210 nm As a result, it was found that three kinds of reaction products were formed by the reaction of lactose with insulin. The reaction products were designated in order of increasing retention time on HPLC as product-3, product-2, and product-1. Insulin showed the longest retention time. The results are shown in Table 1.

TABLE 1

Addition of Lactose to Insulin

|  | Insulin | Product-1 | Product-2 | Product-3 |
|---|---|---|---|---|
| 0 hour | 100% | 0% | 0% | 0% |
| 5 hours | 56% | 35% | 6% | 4% |
| 24 hours | 21% | 32% | 11% | 36% |

The results in Table 1 show that lactose reacts with insulin in a weakly basic solution (pH 8.1) at 40° C. with the passage of time. The proportion of product-1 was high 5 hours after the start of reaction, but after 24 hours, the proportion of product-3 increased.

Example 2

Bovine pancreatic insulin (0.2 mg, Wako Pure Chemical Industries, Ltd.) was dissolved in 1 mL of a 1 mmol/L aqueous solution of hydrochloric acid. To about 25 mg of sialyllactose of 75% purity (a mixture of 3'-sialyllactose and 6'-sialyllactose, Boehringer Mannheim GmbH) was added 0.1 mL of a 600 mmol/L aqueous solution of disodium hydrogenphosphate to make a solution. The insulin solution (0.1 mL) and the sialyllactose solution (0.1 mL) were mixed in a test tube to give a mixture having a pH of about 7.8. The test tube was put into a constant temperature water bath at 40° C. to cause reaction and left for 3 days. The reaction mixture was sampled intermittently, followed by centrifugation at 3000 rpm for 20 minutes to remove insoluble materials. The samples collected 0, 1 and 3 days after the start of the reaction were analyzed for products obtained by the reaction of insulin with sialyllactose by HPLC under the following conditions.

Column: YMC-Pack ODS-AP, 4.6×150 mm

Mobile phase: 20 mmol/L phosphate buffer (pH 8.0) containing 0.001% Triton X-100: acetonitrile containing 0.001% Triton X-100=411 parts by volume: 140 parts by volume Flow rate: 1.3 mL/minute Detection wavelength: 220 nm As a result, it was found that three kinds of reaction products were formed by the reaction of sialyllactose with insulin. The reaction products were designated in order of increasing retention time on HPLC as product-6, product-5, and product-4. Insulin showed the longest retention time. The results are shown in Table 2.

TABLE 2

Addition of Sialyllactose to Insulin

|  | Insulin | Product-4 | Product-5 | Product-6 |
|---|---|---|---|---|
| 0 hour | 100% | 0% | 0% | 0% |
| 1 day | 50% | 12% | 36% | 2% |
| 3 days | 31% | 15% | 52% | 3% |

The results in Table 2 show that sialyllactose reacts with insulin in a weakly basic solution (pH 7.8) at 40° C. with the passage of time. The proportion of product-5 was high as compared with the other products both after 1 day and 3 days and its proportion increased with the passage of time.

Example 3

A solution of 0.1 mg of bovine pancreatic insulin (Sigma Chemical Co.) in 0.1 mL of a 20 mmol/L aqueous solution of hydrochloric acid, a solution of 160 mg of anhydrous β-lactose (Nacalai Tesque, Inc.) in 1 mL of distilled water, and 0.9 mL of a 100 mmol/L phosphate buffer (pH 8.4) were mixed in a test tube. The mixture was subjected to reaction at 37° C. for 24 hours.

Example 4

Bovine pancreatic insulin (0.1 mg, Sigma Chemical Co.) was dissolved in 0.1 mL of a 20 mmol/L aqueous solution of hydrochloric acid. The solution was mixed with 0.9 mL of a 600 mmol/L aqueous solution of disodium hydrogenphosphate in a test tube to obtain a solution to be used as an insulin solution. To about 25 mg of sialyllactose of 75% purity (a mixture of 3'-sialyllactose and 6'-sialyllactose, Boehringer Mannheim GmbH) was added 0.13 mL of distilled water to make a solution. The insulin solution (0.13 mL) and the sialyllactose solution (0.13 mL) were mixed in a test tube, and the mixture was subjected to reaction at 37° C. for 24 hours.

Comparative Example 1

A 20 mmol/L aqueous solution of hydrochloric acid (0.1 mL), 1 ml of distilled water, and 0.9 mL of a 100 mmol/L phosphate buffer (pH 8.4) were mixed in a test tube. The mixture was allowed to stand at 37° C. for 24 hours.

Comparative Example 2

A solution of 0.1 mg of bovine pancreatic insulin (Sigma Chemical Co.) in 0.1 mL of a 20 mmol/L aqueous solution of hydrochloric acid, 1 ml of distilled water, and 0.9 mL of a 100 mmol/L phosphate buffer (pH 8.4) were mixed in a test tube. The mixture was allowed to stand at 37° C. for 24 hours.

Comparative Example 3

A solution of 160 mg of anhydrous e-lactose (Nacalai Tesque, Inc.) in 1 mL of distilled water, 0.1 mL of a 20 mmol/L aqueous solution of hydrochloric acid, and 0.9 ML of a 100 mmol/L phosphate buffer (pH 8.4) were mixed in a test tube. The mixture was allowed to stand at 37° C. for 24 hours to prepare solution A (lactose solution).

In a manner similar to that in Comparative Example 2, a solution of 0.1 mg of bovine pancreatic insulin (Sigma Chemical Co.) in 0.1 mL of a 20 mmol/L aqueous solution of hydrochloric acid, mL of distilled water, and 0.9 mL of a 100 mmol/L phosphate buffer (pH 8.4) were mixed in a test tube. The mixture was allowed to stand at 37° C. for 24 hours to prepare solution B (insulin solution).

Test Example 1

A solution of 0.2 mg of bovine pancreatic insulin (Wako Pure Chemical Industries, ltd.) in 1 mL of a 2 mmol/L aqueous solution of hydrochloric acid, a solution of 320 mg of anhydrous β-lactose (Nacalai Tesque, Inc.) in 2 mL of distilled water, and 1 mL of a 200 mmol/L phosphate buffer (pH 8.4) were mixed in a test tube. The mixture was subjected to reaction at 40° C. for 24 hours. To 3 mL of the resulting solution was added 0.5 mL of a 50 mmol/L aqueous solution of citric acid to adjust the pH to 6.7, and the mixture was subjected to reaction at 40° C. The samples collected from the reaction mixture 0 and 30 minutes after the start of the reaction were analyzed for products obtained by the reaction of insulin with lactose by HPLC in a manner similar to that in Example 1. The results are shown in Table 3.

TABLE 3

Release of Lactose Caused by pH Lowering to 6.7

|  | Insulin | Product-1 | Product-2 | Product-3 |
|---|---|---|---|---|
| 0 minute | 25% | 42% | 13% | 20% |
| 30 minutes | 45% | 18% | 25% | 12% |

As shown in Table 3, the lowering of the pH of the mixture from 8.1 to 6.7 caused release of lactose from the products and increase in the amount of free insulin to which lactose was not bound.

Test Example 2

A solution of 0.2 mg of bovine pancreatic insulin (Wako Pure Chemical Industries, ltd.) in 1 mL of a 2 mmol/L aqueous solution of hydrochloric acid, a solution of 320 mg of anhydrous β-lactose (Nacalai Tesque, Inc.) in 2 mL of distilled water, and 1 mL of a 200 mmol/L phosphate buffer (pH 8.4) were mixed in a test tube. The mixture was subjected to reaction at 40° C. for 24 hours. To 3 mL of the resulting solution was added 0.5 mL of a 100 mmol/L aqueous solution of citric acid to adjust the pH to 5.9, and the mixture was subjected to reaction at 40° C. The reaction mixture was intermittently analyzed for products obtained by the reaction of insulin with lactose by HPLC in a manner similar to that in Example 1. The results are shown in Table 4.

TABLE 4

Release of Lactose Caused by pH Lowering to 5.9

|  | Insulin | Product-1 | Product-2 | Product-3 |
|---|---|---|---|---|
| 0 minute | 24% | 36% | 13% | 27% |
| 2 minutes | 35% | 27% | 22% | 17% |
| 10 minutes | 59% | 5% | 33% | 3% |
| 30 minutes | 76% | 0% | 25% | 0% |
| 60 minutes | 75% | 0% | 25% | 0% |

As shown in Table 4, the lowering of the pH of the mixture from 8.1 to 5.9 caused rapid release of lactose from product-1 and product-3.

Test Example 3

A solution of 0.2 mg of bovine pancreatic insulin (Wako Pure Chemical Industries, ltd.) in 1 mL of a 2 mmol/L aqueous solution of hydrochloric acid, a solution of 320 mg of anhydrous β-lactose (Nacalai Tesque, Inc.) in 2 mL of distilled water, and 1 mL of a 200 mmol/L phosphate buffer (pH 8.4) were mixed in a test tube. The mixture was subjected to reaction at 40° C. for 24 hours. To 3 mL of the resulting solution was added 0.5 mL of a 150 mmol/L aqueous solution of citric acid to adjust the pH to 5.0, and the mixture was subjected to reaction at 40° C. The reaction mixture was intermittently sampled and analyzed for products obtained by the reaction of insulin with lactose by HPLC in a manner similar to that in Example 1. The results are shown in Table 5.

TABLE 5

Release of Lactose Caused by pH Lowering to 5.0

|  | Insulin | Product-1 | Product-2 | Product-3 |
|---|---|---|---|---|
| 0 minute | 21% | 35% | 13% | 32% |
| 2 minutes | 60% | 8% | 27% | 5% |
| 10 minutes | 83% | 0% | 17% | 0% |
| 30 minutes | 93% | 0% | 7% | 0% |
| 60 minutes | 95% | 0% | 5% | 0% |

As shown in Table 5, the lowering of the pH of the mixture from 8.1 to 5.0 caused rapid and almost complete release of lactose from all the products.

Test Example 4

Bovine pancreatic insulin (0.2 mg, Wako Pure Chemical Industries, Ltd.) was dissolved in 1 mL of a 1 mmol/L aqueous solution of hydrochloric acid. To about 25 mg of sialyllactose of 75% purity (a mixture of 3'-sialyllactose and 6'-sialyllactose, Boehringer Mannheim GmbH) was added 0.1 mL of a 600 mmol/L aqueous solution of disodium hydrogenphosphate to make a solution. The insulin solution (0.1 mL) and the sialyllactose solution (0.1 mL) were mixed in a test tube to give a solution having a pH of about 7.8. This solution was subjected to reaction at 40° C. for 3 days and then centrifuged at 3000 rpm for 20 minutes. To 40 μL of the supernatant was added 0.04 mL of a 50 mmol/L-aqueous solution of citric acid to adjust the pH to 6.4, and the resulting solution was subjected to reaction at 40° C. The reaction mixture was intermittently sampled and analyzed for products obtained by the reaction of insulin with sialyllactose by HPLC in a manner similar to that in Example 2. The results are shown in Table 6.

TABLE 6

Release of Sialyllactose Caused by pH Lowering to 6.4

|  | Insulin | Product-4 | Product-5 | Product-6 |
|---|---|---|---|---|
| 0 minute | 31% | 15% | 52% | 3% |
| 10 minutes | 44% | 9% | 43% | 4% |
| 30 minutes | 50% | 6% | 41% | 3% |

Test Example 5

Bovine pancreatic insulin (0.2 mg, Wako Pure Chemical Industries, Ltd.) was dissolved in 1 mL of a 1 mmol/L aqueous solution of hydrochloric acid. To about 25 mg of sialyllactose of 75% purity (a mixture of 3'-sialyllactose and 6'-sialyllactose, Boehringer Mannheim GmbH) was added 0.1 mL of a 600 mmol/L aqueous solution of disodium hydrogenphosphate to make a solution. The insulin solution (0.1 mL) and the sialyllactose solution (0.1 mL) were mixed in a test tube to give a solution having a pH of about 7.8. This solution was subjected to reaction at 40° C. for 3 days and then centrifuged 1 at 3000 rpm for 20 minutes. To 40 μL of the supernatant was added 0.04 mL of a 100 mmol/L aqueous solution of citric acid to adjust the pH to 5.3, and the resulting solution was subjected to reaction at 40° C. The reaction mixture was intermittently sampled and analyzed for products obtained by the reaction of insulin with sialyllactose by HPLC in a manner similar to that in Example 2. The results are shown in Table 7.

TABLE 7

Release of Sialyllactose Caused by pH Lowering to 5.3

|  | Insulin | Product-4 | Product-5 | Product-6 |
|---|---|---|---|---|
| 0 minute | 31% | 15% | 52% | 3% |
| 10 minutes | 58% | 3% | 35% | 4% |
| 30 minutes | 80% | 5% | 12% | 3% |

Test Example 6

Male SD strain rats were fasted for 16 to 20 hours and then anesthetized by intraperitoneal administration of 50 mg/kg pentobarbital sodium, followed by cannulation into the femoral vein and carotid. A cannula was also inserted into the trachea to maintain airway. Five minutes before the administration of each test solution, 0.4 mL of a blood sample was collected through the cannula inserted into the carotid and transferred into a heparin-treated plastic test tube. After the blood sampling, 0.4 mL of physiological saline was put into the carotid through the cannula. The reaction mixtures obtained in Examples 3 and 4 and Comparative Examples 1 and 2 were respectively administered to the rats through the cannula inserted into the femoral vein in an amount of 20 μL for 100 g of body weight. Solution A obtained in Comparative Example 3 was administered through the cannula inserted into the femoral vein in an amount of 20 μL for 100 g of body weight, and immediately thereafter, solution B was intravenously administered in a 1 similar manner. Blood samples (0.4 mL each) were collected through the cannula inserted into the carotid 5, 10, 30, 60 and 120 minutes after the administration of each test solution, and then transferred into heparin-treated plastic test tubes. After each blood sampling, 0.4 mL of physiological saline was put into the carotid through the cannula. The blood samples were centrifuged at 5° C. at 10000 rpm for 5 minutes to obtain plasma. The concentration of insulin in each plasma was determined by enzyme immuno assay using GLAZYME Insulin-EIA Test (Wako Pure Chemical Industries, Ltd.) The results are shown in Table 8.

TABLE 8

Change in Insulin Concentration in Plasma (unit: μU/mL)

| Time (min.) | Comp. Ex. 1 | Comp. Ex. 2 | Comp. Ex. 3 | Ex. 3 | Ex. 4 |
|---|---|---|---|---|---|
| −5 | 23 | 11 | 13 | 17 | 7 |
| 5 | 31 | 476 | 506 | 603 | 589 |
| 10 | 42 | 185 | 186 | 255 | 242 |
| 30 | 22 | 16 | 13 | 46 | 56 |
| 60 | 34 | 8 | 4 | 27 | 23 |
| 120 | 24 | 17 | 15 | 36 | 20 |

As shown in Table 8, when the preparations of Examples 3 and 4 were used, the plasma insulin concentration changed in high regions as compared with the cases where the preparations of Comparative Examples 1 to 3 were used. There was no significant difference between the results obtained with the preparations of Comparative Examples 2 and 3, which indicates that the released lactose does not affect the disappearance of insulin in plasma.

INDUSTRIAL APPLICABILITY

The present invention provides a pharmaceutical preparation which is capable of rapidly releasing a compound having a free amino group such as an amino acid derivative, a peptide, a protein or an enzyme in response to changes in pH at focuses. The preparation of the present invention is capable of improving the in vivo durability of various compounds and releasing the compounds in response to changes in pH, thus enabling the compounds to act specifically on target parts.

The invention claimed is:

1. A pharmaceutical preparation comprising a compound (I), which is obtained by reacting a peptide (II) having a free amino group, with a sugar (III) having reducing power and selected from group A, wherein said peptide is a pharmaceutical compound,
    wherein group A consists of lactose, sialyllactose and compounds prepared by chemically binding a polymer from the group consisting of polyoxyethylene, polyglutamic acid and polyvinylpyrrolidone to a hydroxyl group other than the hydroxyl group formed from the reducing aldehyde group of lactose and sialyllactose,
    wherein an amino group of said peptide (II) reacts with an aldehyde group in said sugar (III); and
    wherein said compound (I) can release said peptide (II) having a free amino group in response to changes in pH.

2. The preparation according to claim 1, wherein said peptide (II) is insulin.

3. The preparation according to claim 1, wherein said peptide (II) is enkephalin.

4. The preparation according to claim 1, wherein said compound (I) is in a pharmaceutical carrier obtained by the following steps:
    said peptide (II) is combined with a pharmaceutical carrier, to obtain a peptide-carrier composition, and said peptide-carrier composition is reacted with said sugar (III) to give said preparation comprising said compound (I).

5. The preparation according to claim 1, wherein said compound (I) is in a pharmaceutical carrier obtained by the following steps:

said peptide (II) is reacted with said sugar (III) to give said compound (I), and said compound (I) is combined with a pharmaceutical carrier.

6. The preparation according to claim 1, wherein said compound (I) is encapsulated in a pharmaceutical carrier obtained by the following steps:
said peptide (II) and said sugar (III) are encapsulated in a pharmaceutical carrier, and said peptide (II) is reacted with said sugar (III) to give said compound (I) in said pharmaceutical carrier.

7. The preparation according to claim 1, wherein said compound (I) is encapsulated in a pharmaceutical carrier obtained by the following steps:
said peptide (II) is reacted with said sugar (III) to give said compound (I), and said compound (I) is encapsulated in said pharmaceutical carrier.

8. The preparation according to any one of claims 4–7, wherein said pharmaceutical carrier is selected from the group consisting of liposome, lipid emulsion, microemulsion, polymer micelle, microcapsule, microsphere and magnetic particles.

9. The preparation according to claim 1, wherein said group A consists of lactose and sialyllactose.

10. The preparation according to any one of claims 4–7, wherein said group A consists of lactose and sialyllactose.

11. The preparation according to claim 8, wherein said group A consists of lactose and sialyllactose.

12. The preparation according to claim 2, wherein said compound (I) is in a pharmaceutical carrier obtained by the following steps:
insulin is combined with a pharmaceutical carrier, to obtain an insulin-carrier composition, and said insulin-carrier composition is reacted with said sugar (III) to give said preparation comprising said compound (I).

13. The preparation according to claim 2, wherein said compound (I) is in a pharmaceutical carrier obtained by the following steps:
insulin is reacted with said sugar (III) to give said compound (I), and said compound (I) is combined with a pharmaceutical carrier.

14. The preparation according to claim 2, wherein said compound (I) is encapsulated in a pharmaceutical carrier obtained by the following steps:
insulin and said sugar (III) are encapsulated in a pharmaceutical carrier, and said insulin is reacted with said sugar (III) to give said compound (I) in said pharmaceutical carrier.

15. The preparation according to claim 2, wherein said compound (I) is encapsulated in a pharmaceutical carrier obtained by the following steps:
insulin is reacted with said sugar (III) to give said compound (I), and said compound (I) is encapsulated in said pharmaceutical carrier.

16. The preparation according to any one of claims 12–15, wherein said pharmaceutical carrier is selected from the group consisting of liposome, lipid emulsion, microemulsion, polymer micelle, microcapsule, microsphere and magnetic particles.

17. The preparation according to claim 3, wherein said compound (I) is in a pharmaceutical carrier obtained by the following steps:
enkephalin is combined with a pharmaceutical carrier, to obtain an enkephalin-carrier composition, and said enkephalin-carrier composition is reacted with said sugar (III) to give said preparation comprising said compound (I).

18. The preparation according to claim 3, wherein said compound (I) is in a pharmaceutical carrier obtained by the following steps:
enkephalin is reacted with said sugar (III) to give said compound (I), and said compound (I) is combined with a pharmaceutical carrier.

19. The preparation according to claim 3, wherein said compound (I) is encapsulated in a pharmaceutical carrier obtained by the following steps:
enkephalin and said sugar (III) are encapsulated in a pharmaceutical carrier, and said enkephalin is reacted with said sugar (III) to give said compound (I) in said pharmaceutical carrier.

20. The preparation according to claim 3, wherein said compound (I) is encapsulated in a pharmaceutical carrier obtained by the following steps:
enkephalin is reacted with said sugar (III) to give said compound (I), and said compound (I) is encapsulated in said pharmaceutical carrier.

21. The preparation according to any one of claims 17–20, wherein said pharmaceutical carrier is selected from the group consisting of liposome, lipid emulsion, microemulsion, polymer micelle, microcapsule, microsphere and magnetic particles.

* * * * *